United States Patent [19]

Forte et al.

[11] 4,353,135
[45] Oct. 12, 1982

[54] PATELLAR FLANGE AND FEMORAL KNEE-JOINT PROSTHESIS

[75] Inventors: Mark R. Forte, Pine Brook, N.J.; David A. Sonstegard, Hudson, Wis.

[73] Assignee: Minnesota Mining and Manufacturing Company, St. Paul, Minn.

[21] Appl. No.: 148,291

[22] Filed: May 9, 1980

[51] Int. Cl.$^3$ ............................................. A61F 1/03
[52] U.S. Cl. .................................. 3/1.911; 128/92 C
[58] Field of Search ........................... 3/1.911, 1.91; 128/92 C

[56] References Cited

U.S. PATENT DOCUMENTS

| | | | |
|---|---|---|---|
| 3,696,446 | 10/1972 | Bousquet et al. | 3/1.128 |
| 3,715,763 | 2/1973 | Link | 3/1.128 |
| 3,728,742 | 4/1973 | Averill et al. | 3/1.128 |
| 3,748,662 | 7/1973 | Helfet | 3/1.128 |
| 3,774,244 | 11/1973 | Walker | 3/1.128 |
| 3,806,961 | 4/1974 | Muller | 128/92 C X |
| 3,816,855 | 6/1974 | Saleh | 3/1.128 |
| 3,869,731 | 3/1975 | Waugh et al. | 3/1.128 |
| 3,878,566 | 4/1975 | Bechtol | 3/1.91 |
| 3,918,101 | 11/1975 | LaGrange et al. | 3/1.911 |
| 3,924,277 | 12/1975 | Reykers et al. | 3/1.911 |
| 3,927,423 | 12/1975 | Swanson | 3/1.91 |
| 3,946,445 | 3/1976 | Bentley et al. | |
| 3,964,106 | 6/1976 | Hutter et al. | 3/1.911 |
| 4,001,896 | 1/1977 | Arkangel | 3/1.91 |
| 4,007,495 | 2/1977 | Frazier | 3/1.91 |
| 4,016,606 | 4/1977 | Murray et al. | 3/1.911 |
| 4,041,550 | 8/1977 | Frazier | 3/1.91 |
| 4,081,866 | 4/1978 | Upshaw et al. | 3/1.911 |
| 4,094,017 | 6/1978 | Matthews et al. | 3/1.911 |
| 4,136,405 | 1/1979 | Pastrick et al. | 3/1.911 |
| 4,151,615 | 5/1979 | Hall | 3/1.91 |
| 4,158,894 | 6/1979 | Worrell | 3/1.91 |
| 4,262,368 | 4/1981 | Lacey | 3/1.911 |

*Primary Examiner*—Clifford D. Crowder
*Attorney, Agent, or Firm*—Cruzan Alexander; Donald M. Sell; Gary L. Griswold

[57] ABSTRACT

A patellar flange for a knee joint prosthesis comprising a curved base and a pair of condylar runners, one of said condylar runners being attached to each lateral side of the base and extending outwardly anteriorly therefrom diverging from each other and converging to the base superiorly and a femoral knee joint prosthesis containing the flange.

6 Claims, 11 Drawing Figures

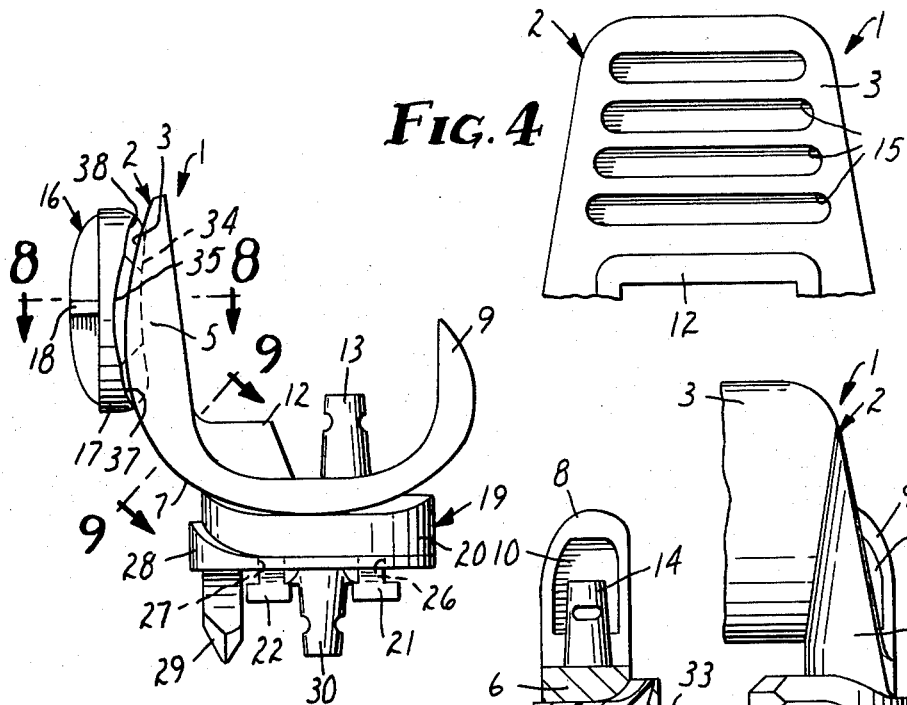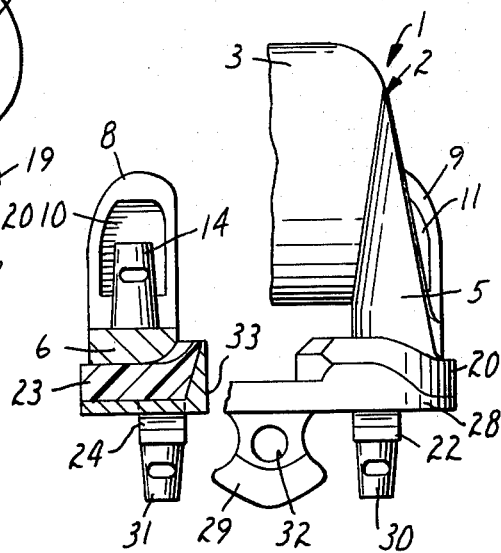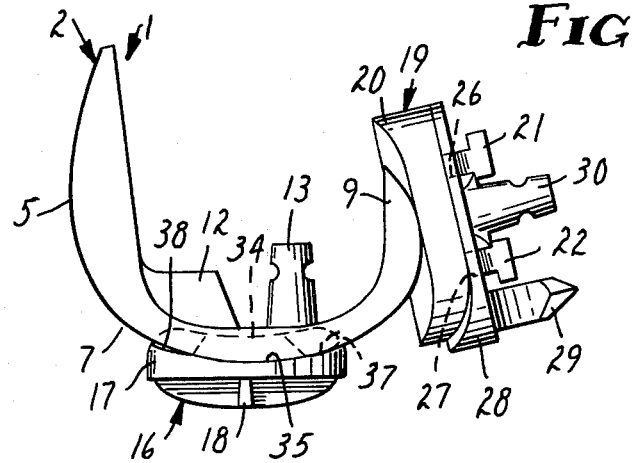

PATELLAR FLANGE AND FEMORAL KNEE-JOINT PROSTHESIS

This invention relates to a knee-joint prosthesis, specifically to the femoral portion of the knee-joint prosthesis and even more particularly to the patellar flange of the femoral prosthesis.

Two general types of knee prosthetic devices are available. The first type is a total knee joint which replaces the femoral and tibial components of the knee joint. With this type of prosthesis the cruciate ligaments are removed. Additionally with this type of prosthesis a portion or all of the patella is sometimes retained and the patellar contacting surface of the femoral component of the prosthesis is sometimes grooved to receive the natural patella or patellar prosthetic device and provide a surface for tracking of the patella device. Prostheses of the total knee-joint type are shown in U.S. Pat. Nos. 3,696,446; 3,918,101; 4,001,896; 4,016,606; 4,094,017 and 4,136,405. The prosthesis depicted in U.S. Pat. No. 4,016,606 contains a vertical groove for patellar movement and is described as being not "handed" in that it will either fit a right or a left knee.

In other knee joint prostheses the tibia and femur are resurfaced at the knee joint and the tibial and femoral components are generally provided with openings for the cruciate ligaments. In certain of these devices a femoral flange is provided which has a groove or a zone of contact for the natural patella or for a patella prosthetic device. Prostheses of this type are shown in U.S. Pat. Nos. 3,816,855; 3,869,731; 3,924,277; 3,964,106; 4,007,495; 4,041,550, 4,081,866; 4,151,615 and 4,158,894. Prostheses of this type are also described in U.S. patent applications Averill, Ser. No. 912,075, filing date June 8, 1978 and Averill, Ser. No. 27,518, filing date Apr. 5, 1979.

A knee-joint prosthesis having a patellar flange which is "nonhanded" and which provides adequate movement for the patella without audible sound was heretofore unknown. Applicants have discovered such a flange. It is a patellar flange for a knee-joint prosthesis comprising (1) a curved base having a radius of curvature substantially the same as the base of the femoral patellar notch of the natural human knee, said base being sufficiently long and wide superiorly to provide a contacting surface for the patella when the knee is in full extension, and (2) a pair of condylar runners, one of said condylar runners being attached to each lateral side of the base and extending outwardly anteriorly from said base, said condylar runners diverging from each other and converging to said base as they proceed superiorly on said base and being of sufficient length to provide a contacting surface for the patella as the knee is flexed.

The patellar flange of the present invention can be used either with the hinged type knee-joint prosthesis or can be used with a resurfacing type knee-joint prosthesis. The preferred usage of the patellar flange of this invention is as part of the femoral prosthesis of the resurfacing type.

A preferred embodiment of the present invention as well as the method of use of the present invention will be discussed below in more detail in reference to the following drawings in which FIG. 1 is a front or anterior view of the femoral component of a knee-joint prosthesis of the present invention containing an embodiment of the patellar flange of the present invention;

FIG. 4 is a posterior or back view of the patellar flange portion of the femoral prosthesis of FIG. 1;

FIG. 5 is a side view of a knee prosthesis at full extension including a prosthetic patella, the femoral prosthesis of FIG. 1 and a tibial component;

FIG. 6 is a side view of the knee of FIG. 5 at 100° flexion;

FIG. 7 is an anterior or front view of the femoral and tibial components of the knee prosthesis of FIG. 5 with parts removed and parts in section;

Figure 1:
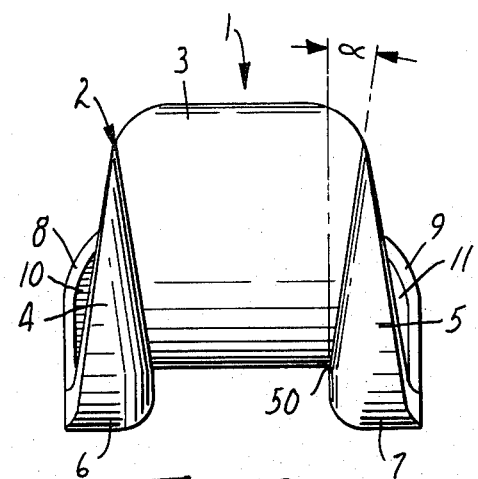

Referring now to the figures in more detail, in FIG. 1 a front or anterior view of the femoral prosthesis 1 containing patellar flange 2 is shown. The patellar flange 2 comprises base 3 and condylar runners 4 and 5 attached at each of the lateral sides of the base 3. Condylar runners 4 and 5 extend outwardly anteriorly from base 3 and diverge at angle alpha. Alpha is normally from 6° to 12°, preferably 8° to 10° to accommodate the anatomy and biomechanical characteristics of natural bone. Angle alpha is the angle of divergence relative to a line parallel to the vertical axis of the flange 2 and contacting the point 50 at which divergence begins. Normally the condylar runners 5, 4 will commence diverging at about the inferior end of the patellar flange 2. The symmetrical divergence of condylar runners 4, 5 allows the patellar flange 2 of the present invention to be used in either the left or the right knee; i.e., to be nonhanded. It also provides for a smooth transition of the patella during flexion without any audible sound. Connected to condylar runners 4 and 5 are distal condylar members 6, 7 and posterior condylar members 8 and 9 attached to distal condylar members 6 and 7. Base 3 of patella flange 2 has a radius of curvature which approximates that of the base of the femoral patellar notch of the natural knee joint and is of a sufficient height and width to provide a track for the patella in either a left or right knee, as will be discussed in more detail later, at a point of full extension of the knee joint. Posterior condylar members 8 and 9 include indentations 10 and 11 respectively, for receipt of bone cement which is placed in these indentations when the femoral prosthesis 1 is placed on the femoral portion of the knee during implantation. Such placement and attachment occurs after the femoral portion is resected and drilled following normal orthopedic surgical procedures.

Figure 2:
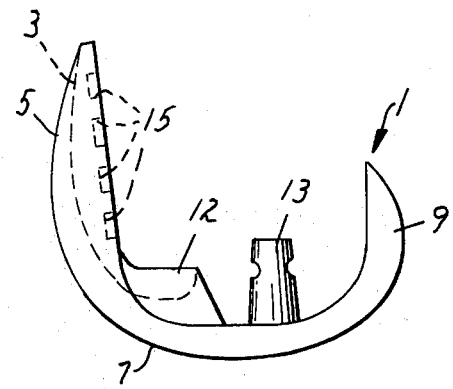
FIG. 2 is a side view of the femoral prosthesis of FIG. 1.

The femoral prosthesis 1 is shown in side view in FIG. 2. In this view, in addition to the previously discussed features, it can also be seen that the distal condylar members are joined by bridge 12 and that distal condylar member 7 contains on its superior surface a peg 14 which is implanted in the femoral portion of the knee in holes which are drilled prior to implantation. Distal condylar member 6 contains a similar peg which is not shown. As can be seen in FIG. 2, via the dotted line, condylar runner 5 (and correspondingly condylar runner 4) converges to the base 3 as it proceeds superiorly on base 3. It is also apparent from FIG. 2 that the radius of curvature of condylar runner 5 (and 4) has a radius of curvature different from that of base 3. This and the diverging characteristic provide the smooth transition of the patella during flexure of the knee. An example of the radius of curvature of the base 3 is about 2¼ inches or 57.2 millimeters. An example of the condylar runner radius of curvature at the patellar flange 2 is about 1½ inches or 38.1 millimeters. Of course radius of curvature is relevant only if the center point is established, thus the aforementioned radii are presented for a relative comparison but are center point dependent. Base 3, on its back surface, contains indentations 15 which are included for receipt of cement which secures the femoral prosthesis onto the end of the femur.

Figure 3:
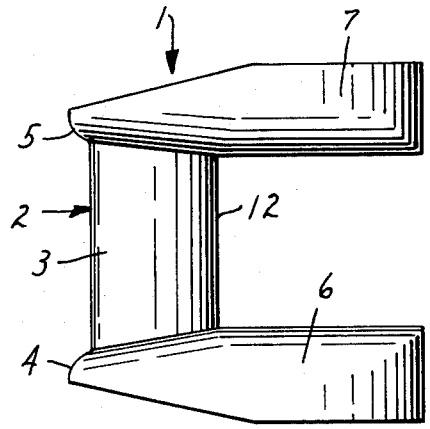
FIG. 3 is a bottom view of the femoral prosthesis of FIG. 1.

The bottom or inferior surface of the femoral prosthesis is shown in FIG. 3. In this view, the bottom portion of the bridge 12 can be seen as well as the bottom portion of distal condylar members 6 and 7 and condylar runners 4 and 5. The space between distal condylar members 6 and 7 provides the area into which the cruciate ligaments reside when this resurfacing type femoral prosthesis is placed in the knee. FIG. 4, which is a partial back view of the patellar flange 2, shows the extent to which the cement receiving indentations 15 in the base 3 extend.

FIGS. 5 and 7 depict the three components of the knee-joint prosthesis for resurfacing of the tibia, femur, and the patella after normal resecting and drilling or reaming thereof. Femoral prosthesis 1 is as described with respect to FIGS. 1 through 4. This view depicts the knee in full extension with the patellar component 16 at the most superior position on base 3. The details of the patellar component will be described in more detail in respect to FIGS. 8 through 11. It comprises polymeric bearing portion 17 and metallic affixing portion 18. The tibial component 19 comprises polymeric bearing portion 20 which is held in place by projections 21, 22. There is a corresponding polymeric bearing portion 23 on the other lateral surface of the tibial component which is held in place by tab 24 and another tab which is not shown. Tabs 21 and 22 pass through holes 26, 27 through base 28. Base 28 contains projection 29 which, along with pegs 30 and 31 are for securement of the tibial component 19 on the tibia of the natural knee. Projection 29 contains hole 32 to allow for tissue ingrowth or for the inclusion of cement. Behind base 28 at the point where projection 29 is attached is a space 33 through which the cruciate ligaments of the natural knee pass.

FIG. 6 depicts the combination of the femoral prosthesis 1, patella component 16 and tibial component 19 with the knee joint flexed approximately 100°. This causes the bearing portion 20 of tibial component 19 to move to the posterior condylar member 9 and causes the patellar component 16 to move to the distal condylar member 7 of femoral prosthesis 1. The other symmetrical side of each component is likewise oriented.

Figure 8:
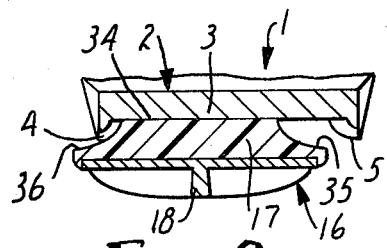
FIG. 8 is a section view taken along line 8—8 of FIG. 5.

FIG. 8 indicates the location of patellar component 16 in the full extension position on a right-hand knee. As can be seen, the patellar component 16 is closest to condylar runner 4, because on the right knee the patellar component 16 will move to the outside condyle. With a left-hand knee, patellar component 16 would also move to the outside condyle runner, which, in that instance, would be runner 5. At full extension the polymeric bearing portion 17 of the patellar component is contacting the base 3 of the patellar flange 2 at curved portion 34. Shoulders 35, 36 of patellar component 16 do not contact the flange except to the extent that a portion of shoulder 36 may contact condylar runner 4 if the patellar component 16 moves that far laterally.

Figure 9:
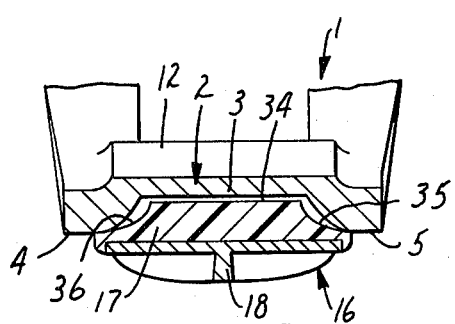
FIG. 9 is a section view taken along line 9—9 of FIG. 5.

FIG. 9 depicts the patellar component 16 as it would be with 45° to 50° flexion of the knee. In this case the curved portion 34 of the patellar component 16 is not in contact with base 3 of patellar flange 2. Instead, the patellar component in moving inferiorly on the patellar flange 2 has contacted, via its shoulders 35, 36 the converging and rising condylar runners 5 and 4 respectively, thus lifting the patellar component 16 so that curved portion 34 is no longer in contact with base 3. Normally the shoulders 35, 36 and converging and rising condylar runners 5 and 4 cause the patellar component 16 to move anteriorly a sufficient distance so that curved portion 34 no longer is in contact with base 3 when the knee is flexed at least about 15°. This may vary from individual to individual. The dual tracking provided with the femoral prosthesis 1 and patellar component 16 provides latitude for patient variability in muscle as well as skeleton and provides the surgeon with a degree of forgiveness of alignment. As the knee is flexed more load is placed on patellar component 16. As more load is placed on patellar component 16 it is correspondingly more restrictedly tracked between and on converging condylar runners 5 and 4 via shoulders 35 and 36.

Figure 10:
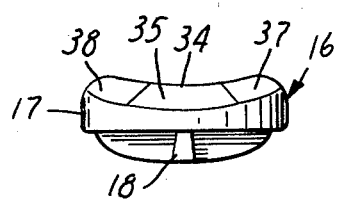
FIG. 10 is a side view of the prosthetic patella of FIG. 5.
Figure 11:
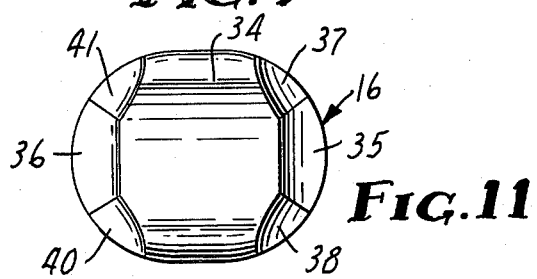
FIG. 11 is a view of the patellar flange contacting portion or portion surface of the prosthetic patella of FIG. 10.

FIGS. 10 and 11 depict the patellar component 16 laterally and posteriorly and depicts the curved portion 34 of polymeric bearing portion 17 and metallic affixing portion 18. Also shown are the rounded corners 37, 38, 40, 41 and shoulders 35, 36 between the rounded corners 37, 38, 40, 41. Shoulders 35, 36 are the portions which ride on the condylar runners 5 and 4, respectively, of patellar flange 2. The rounded corners 37, 38, 40, 41 cause the patellar component to slide more easily without noise on the patellar flange 2.

The polymeric bearing portion 17 of patellar component 16, as discussed, rides on patellar flange 2. Metallic affixing portion 18 of the patellar component is cemented to a resected and grooved natural patella.

The polymeric portions of the knee prosthesis as depicted are made from polymeric material, for example, "Teflon" brand fluorocarbon polymers or ultrahigh molecular weight polyethylene. Other physiologically acceptable polymeric materials can also be used. The other portions of the prosthesis are made of physiologically acceptable metals or metal alloys such as cobalt/chromium/molybdenum containing steel. The various components of the prosthesis are manufactured using conventional techniques for making prosthetic devices including projection molding of polymeric parts and investment casting of metal parts.

What is claimed is:

1. A patellar flange for a knee-joint prosthesis comprising (1) a curved base having a radius of curvature substantially the same as the base of the femoral patellar notch of the natural human knee, said base being sufficiently long and wide superiorly to provide a contacting surface for the patella when the knee is in full extension, and (2) a pair of condylar runners, one of said condylar runners being attached to each lateral side of the base and extending outwardly anteriorly from said base, said condylar runners diverging from each other and converging to said base as they proceed superiorly on said base and being of sufficient length to provide a contacting surface for the patella as the knee is flexed.

2. The patellar flange of claim 1 wherein the anterior face of the condylar runner on each lateral side of the base is of a sufficient distance anteriorly from the base and one of the condylar runners is a sufficient distance from the other condylar runner so that the patella contacts only the condylar runners when the knee is flexed at least about 15°.

3. The patellar flange of claim 1 wherein the condylar runners diverge superiorly at from 6° to 12° relative to a line parallel to the vertical axis of the flange and contacting the point where the condylar runners commence diverging.

4. A femoral knee joint prosthesis comprising (1) a patellar flange for a knee-joint prosthesis comprising (a) a curved base having a radius of curvature substantially the same as the base of the femoral patellar notch of the natural human knee, said base being sufficiently long and wide superiorly to provide a contacting surface for the patella when the knee is in full extension, and (b) a pair of condylar runners, one of said condylar runners being attached to each lateral side of the base and extending outwardly anteriorly from said base, said condylar runners diverging from each other and converging to said base as they proceed superiorly on said base and being of sufficient length to provide a contacting surface for the patella as the knee is flexed, (2) a pair of distal condylar members, one of said distal condylar members being attached to the inferior end of each condylar runner, said distal condylar members being attached to each other laterally, and (3) a pair of posterior condylar members, one of said posterior condylar members being attached to each of said distal condylar members at the posterior end thereof.

5. The femoral knee joint prosthesis of claim 4 wherein the anterior face of the condylar runners on each lateral side of the base of the patellar flange is a sufficient distance anteriorly from the base and one of the condylar runners is a sufficient distance from the other condylar runner so that the patella contacts only the condylar runners when the knee is flexed at least about 15°.

6. The femoral knee-joint prosthesis of claim 4 wherein the condylar runners of the patellar flange diverge superiorly at from 6° to 12° relative to a line parallel to the vertical axis of the flange and contacting the point where the condylar runners commence diverging.

* * * * *